United States Patent [19]

Matsuda et al.

[11] 4,273,761
[45] Jun. 16, 1981

[54] METHOD OF ENHANCING ABSORPTION OF ANTITUMOR AGENT INTO GASTROINTESTINAL TUMOR SITE AND ORALLY ADMINISTRABLE ANTITUMOR COMPOSITIONS THEREFOR

[75] Inventors: Akira Matsuda, Omiya; Osamu Yoshioka, Yono; Katsutoshi Takahashi, Tokyo; Kooichi Yoshida, Soka; Hiroshi Ninomiya, Sayama, all of Japan

[73] Assignee: Nippon Kayaku Kabushiki Kaisha, Tokyo, Japan

[21] Appl. No.: 894,844

[22] Filed: Apr. 10, 1978

[30] Foreign Application Priority Data

Apr. 12, 1977 [JP] Japan ................................ 52-41687
Jul. 14, 1977 [JP] Japan ................................ 52-83528

[51] Int. Cl.$^3$ ............................................ A61K 31/78
[52] U.S. Cl. .................................... 424/81; 424/251
[58] Field of Search .................................. 424/81, 251

[56] References Cited

U.S. PATENT DOCUMENTS 2,802,005  8/1957  Heidelberger ...................... 544/313

FOREIGN PATENT DOCUMENTS 256852  6/1963  Australia .
2017409  10/1971  Fed. Rep. of Germany ............. 424/81
51-142523  8/1976  Japan .

OTHER PUBLICATIONS

C.A.; vol. 83, (1975) 84887u.
C.A.; vol. 82 (1975) 103,163c.

Primary Examiner—Allen J. Robinson
Attorney, Agent, or Firm—Russell & Nields

[57] ABSTRACT

This invention relates to a method for selectively enhancing absorption of 5-fluorouracil, bleomycins or bleomycin derivatives into the gastrointestinal tumor site by orally administering such substance together with an alkali metal salt of polyacrylic acid, and an orally administable antitumor composition used for such method.

12 Claims, No Drawings

METHOD OF ENHANCING ABSORPTION OF ANTITUMOR AGENT INTO GASTROINTESTINAL TUMOR SITE AND ORALLY ADMINISTRABLE ANTITUMOR COMPOSITIONS THEREFOR

BACKGROUND OF INVENTION 5-fluorouracil (hereinafter referred to simply as 5-Fu), which is one of the active compounds used in this invention, is a commercially available antitumor agent which is used for treatment of tumors in the digestive organs through peroral administration in the form of an aqueous solution. However, 5-Fu absorbed through the stomach wall tends to amass not only in the tumor site but also in the bone marrow, so that it may cause myeloid trouble. For this reason, the dosage of this medicine is limited although the effect thereof is considerably sacrificed by such limitation. A strong request is therefore voiced in the art for the development of a method which is capable of effecting as much absorption of the medicine into the tumor site as required for tumor treatment while minimizing amassing of the medicine in the bone marrow.

Bleomycin and bleomycin derivatives are also known to have the antitumor activities as for instance disclosed in U.K. Pat. No. 1,038,242, U.S. Pat. No. 3,846,400 and U.S. Pat. No. 3,922,262. However, such bleomycins are scarcely absorbed through the gastroenteric wall, so that the commercially produced bleomycins are exclusively used as injections. Since bleomycins have the inclination to be selectively absorbed into the tumor sites such as skin cancer, head and neck cancers (such as cancer of the upper jaw, cancer of tongue, cancer of lip, laryngeal cancer, etc.), esophagus cancer of squamous epithelium), cervix cancer, malignant lymphoma, glioma, etc., they are used by injection for treatment of these tumors. However, if such bleomycins can be selectively absorbed into the tumors in the digestive organs such as gastrointestinal organs, they can as well be used for treatment of such tumors, so that the development of a method for allowing selective absorption of bleomycins into such tumors is wished.

In the course of extensive studies on this subject, the present inventors have noted quite unexpectedly the facts that when 5-Fu, bleomycin or a bleomycin derivative is perorally administered along with a polyacrylic acid alkali metal salt to the rate having experimentally transplanted gastrointestinal tumors, the concentration of said active compound in the tumors becomes higher than when an aqueous solution of such compound is administered perorally or by subcutaneous injection, and such high concentration is maintained for a long time, in other words, the absorption of said compound is administered perorally or by subcutaneous injection, and such high concentration is maintained for a long time, in other words, the absorption of said compound into the tumors is selectively enhanced to markedly arrest growth of the experimental tumors, and particularly in the case of 5-Fu, the side effects such as myeloid trouble are strikingly suppressed. The present invention was completed on the basis of such findings.

Applications of alkali metal salts of polyacrylic acid as an adjuvant for the medicinal compositions are noted in Australian Pat. No. 256,852 and Japanese Pat. Laid-Open No. 142523/1976. Australian Pat. No. 256,852 discloses a composition comprising tetracycline antibiotics and a hydrolyzed polyacrylonitrile, a polyacrylic acid or salts of any of these compounds for enhancing absorption of tetracycline antibiotics from the stomach and intestines and also elevating their concentration in the blood. Japanese Patent Laid-Open No. 142423/76 discloses a medicinal composition prepared by first forming small granules of a composition comprising the active compound and a water-soluble high molecular material (such as an alkali metal salt of polyacrylic acid, polyethylene glycol, etc.) which forms a highly viscous solution in the presence of water, and then coating these granules with a coating agent which is disintegrated in the stomach. This medicinal composition allows long-time intragastric retention of the medicine which produces strong potency when staying in the stomach for a long time, such as for example antiulcer drugs like antipeptic agents, penicillins, vitamins, etc.

However, none of these prior art literatures shows any disclosure suggestive of the peroral antitumor compositions of this invention comprising 5-Fu, bleomycin or a bleomycin derivative and an alkali metal salt of polyacrylic acid and the fact that such compositions are capable of selectively enhancing absorption of 5-Fu, bleomycin or bleomycin derivatives into the gastrointestinal tumor site.

SUMMARY OF INVENTION

This invention relates to a method for selectively enhancing absorption of 5-Fu, bleomycin or bleomycin derivatives into the gastrointestinal tumor site, and a peroral antitumor composition used in such method. More particularly, this invention relates to a method for increasing the rate of absorption of the active compound into the gastrointestinal tumor site by perorally administering an effective amount of at least one active compound selected from 5-Fu, bleomycins and bleomycin derivatives along with a sufficient amount of an alkali metal salt of polyacrylic acid to attain the desired increase of absorption rate of said compound into the tumor site, and the peroral antitumor medicinal composition comprising an effective amount of at least one active compound selected from 5-Fu, bleomycins and bleomycin derivatives, a polyacrylic acid alkali metal salt of an amount sufficient to provide a desired increase of absorption rate of said compound into the gastrointestinal tumor site, and an adjuvant of the type commonly used for medicinal preparations. The object of this invention is to selectively enhance absorption of said active compound into the gastrointestinal tumor site to elevate the tumor remedial effect of the compound. In case of using 5-Fu as said active compound, it is also envisaged to reduce the side effects of the medicine.

The alkali metal salt of polyacrylic acid used in this invention may be, for example, sodium salts or potassium salts of polyacrylic acid with molecular weight within the range of 1,000,000 to 10,000,000, preferably 3,000,000 to 6,000,000, but sodium salts are most preferred.

The amount of the alkali metal salt of polyacrylic acid used in this invention may be suitably selected within the range of amount capable of providing desired enhancement of selective absorption of said active compound into the gastrointestinal tumor site. More definitely, such amount, although varying depending on the type of the medicine used, is usually within the range of 0.5 to 20 parts (by weight), preferably 1 to 8 parts (by weight), per one part of the active compound.

The bleomycins or bleomycin derivatives used in this invention may be the bleomycins or acid-addition salts thereof obtained from the fermentation process described in British Pat. No. 1,038,242 or the bleomycin derivatives shown in U.S. Pat. No. 3,922,262 and U.S. Pat. No. 3,846,400.

The "adjuvant" employed in this invention may be of any type commonly used for medicinal preparations, such as for example pharmaceutical excipients, binding agents, disintegrators, sweetenings, etc., exclusive of the said active compounds.

DETAILED DESCRIPTION OF INVENTION

The antitumor composition of this invention is usually formulated into the pertinent dosage forms such as mentioned below so as to facilitate dispersion of the composition in the digestive organ.

(1) Granules—the granules formed from a mixture of said active ingredient compound(s), an alkali metal salt of polyacrylic acid and adjuvant(s) are coated with a coating which is insoluble in water but permeable to water so that the granules won't adhere to each other to form lumps but stay separately from each other so that they may be well dispersed in the digestive organs.

(2) Powder and granules—composed of said active compound(s), an alkali metal salt of polyacrylic acid and a large quantity of adjuvant(s) and prepared such that the particles of an alkali metal salt of polyacrylic acid won't adhere to each other to form lumps and that the composition will be well dispersed in the digestive organs.

(3) Tablets—prepared such that they are disintegrated and dispersed by getting the better of water absorptivity an alkali metal salt of polyacrylic acid.

(4) Effervescent tablets or granules—comprising an alkali metal salt of polyacrylic acid and active compound(s) as well as an effervescent component.

The amount of the active compound(s) in the composition of this invention is usually within the range of 1 to 30% (by weight), preferably 3 to 20%, most preferably 5 to 15% (by weight), and the amount of the alkali metal salt of polyacrylic acid is preferably within the range of 5 to 90%, most preferably 10 to 80% (by weight). The adjuvant is usually added in an amount of 94 to 2%, preferably 90 to 5%, more preferably 85 to 10% (by weight).

The above-said formulated preparations are produced in the following ways.

(1) Formulation of coated granules

An active compound and an alkali metal salt of polyacrylic acid are mixed and powdered and, if need be, further added with an excipient, binding agent and/or other adjuvants and the mixture is granulated by a known method, and then the thus obtained granules are coated with a water-insoluble but water-permeable coating agent dissolved in a solvent. Alternatively, a gel may be formed from said active compound and an alkali metal salt of polyacrylic acid, and after drying and pulverization, the formed granules may be coated with coating agent which form a water-insoluble but water-permeable coating by using, for example, a fluidized bed coating apparatus, and if need be, the granules may be further added with an excipient such as lactose, crystalline lactose, mannitol, powdered sucrose, microcrystalline cellulose, carboxymethyl cellulose, etc. The binding agents usable in this invention include, for example, polyvinyl pyrrolidone, hydroxypropyl cellulose, hydroxypropylmethyl cellulose and the like.

As examples of said coating agents usable in this invention, the following may be cited: ethyl cellulose, cellulose acetate phthalate, hydroxypropylmethyl cellulose phthalate, acrylic acid-methacrylic acid-vinylpyridine copolymers, polyvinyl acetate, methacrylic acid-methacrylic ester copolymers, and methyl acrylate methacrylic acid-methyl methacrylate copolymers.

(2) Formulation of powder and granules

For formulating powder, the active ingredient compound and an alkali metal salt of polyacrylic acid are powdered and added with crystalline lactose, powdered lactose, mannitol, refined sucrose, sorbitol or the like, and the blend is uniformly mixed.

In the case of granules, the powdered active compound and an alkali metal salt of polyacrylic acid are blended with powdered lactose, mannitol, refined sucrose, sorbitol or the like and, after uniform mixing, further added with a binding agent which is soluble in water and organic solvents, such as hydroxypropyl cellulose, hydroxypropyl methyl cellulose, polyvinyl pyrrolidone, etc., and then the blend is formed into granules according to a normal method. The ratio of an alkali metal salt of polyacrylic acid:excipient is preferably greater than 1:2 in the case of powder and greater than 1:3 in the case of granules.

(3) Formulation of tablets

The disintegrating agent used for the formulation of tablets in this invention may be of any known type, but it is preferred to use such agent in a slightly greater amount than normally used for the preparation of ordinary types of tablets. More definitely, the disintegrating agent in this invention is preferably loaded in an amount of at least 20% of an alkali metal salt of polyacrylic acid or the graules containing such salt. Preferred examples of disintegrating agent for use in the composition of this invention are avicel ® (microcrystalline cellulose), starches such as corn starch or potato starch, carboxymethyl cellulose and its calcium salts, and the like.

For producing the tablets according to these regulations, the active compound, an alkali metal salt of polyacrylic acid and an excipient with good fluidity such as crystalline lactose, calcium hydrogen phosphate or previously granulated lactose are mixed, and this mixture is then added with one or two types of disintegrating agent and, if need be, a silicate anhydride (of high specific gravity grade) for fluidizing the mixture, and after further adding a lubricant such as magnesium stearate or talc, the mixture is directly molded into tablets. Alternatively, the granules formed by using a large quantity of excipient may be mixed with one or two types of disintegrating agent and, if need be, a slicate anhydride (of the above-said type) for the purpose of fluidization, and after further adding a lubricant such as magnesium stearate or talc, the mixture may be molded into tablets. The thus obtained tablet, when put into water, is disintegrated and dispersed in a moment, and if agitated slowly, the tablet is well dispersed in water and forms no lump.

(4) Formulation of effervescent granules and tablets

The effervescent granules and effervescent tablets can be produced by combining the granules composed of an active compound, an alkali metal salt of polyacrylic acid and a large quantity of excipient and the granules which quickly produce carbon dioxide gas upon contact with water. The granules which quickly produce carbon dioxide gas upon contact with water comprise the granules composed of a carbonate (usually sodium bicarbonate is used), an excipient and a binding agent and the granules composed of an organic acid such as tartaric acid, citric acid, maric acid, fumaric acid, succinic acid, etc., an excipient and a binding agent. These three types of granules may be simply mixed at suitable proportions to form effervescent granules, or they may be further added with a lubricant and molded into tablets. The advantageous effect of these effervescent preparations is not merely limited to prevention of mutual adhesion of the particles of an alkali metal salt of polyacrylic acid; if the patient is instructed to try to stifle belching so that the stomach cavity is inflated, excellent attachment of the active compound and an alkali metal salt of polyacrylic acid to the stomach wall can be provided.

Peroral administration of the antitumor composition of this invention to man or animal induces selective enhancement of absorption of 5-fluorouracil, bleomycin or bleomycin derivatives into the gastrointestinal tumor. The dosage of the active compound for peroral administration can not be definitely specified as it is subject to change depending on the type of the compound, condition of the disease, human race, class of animal and other factors, but the range of dosage for normal applications is considered to be 0.1 to 10 mg/kg per day. In the case of 5-fluorouracil, the dosage range of preferably 1 to 10 mg/kg, more preferably 2 to 6 mg/kg, is suggested, and in the case of bleomycins, the effective dosage is considered to be within the range of 0.2 to 4 mg/kg, more preferably 0.3 to 2 mg/kg.

The invention is now described in further detail by way of Examples thereof. In the following descriptions of Examples, "5-Fu" is 5-fluorouracil, "PANA" is sodium polyacrylate, "BLM" is bleomycin(s) and "part" means by weight.

EXAMPLE 1 (ANIMAL EXPERIMENT)

1. Preparation of Samples

Sample 1: 5-Fu solution (control)
 Prepared by making a 10% aqueous solution of 5-Fu.
Sample 2: Coated granules of 5-Fu and PANA (5%) (product of this invention).
 5 parts of PANA powder having molecular weight of approximately 5,500,000 and passed through a 150-mesh screen, 10 parts of 5-Fu, 77 parts of mannitol and 3 parts of hydroxypropyl cellulose are mixed uniformly, and the mixture is granulated with an extruction granulator with 0.5 mm extruding pores by using 25 parts of official ethanol, and after drying, the granules are passed through a 24-mesh sieve and a 42-mesh sieve to regulate the grain size. The thus obtained granules are then coated with a coating solution comprising 5 parts of ethyl cellulose (with viscosity of 10 c.p.s.), 1 part of triacetin, 47 parts of ethanol and 47 parts of methylene chloride, the coating being performed such that 95 parts of said granules will become 100 parts in the finished form, and the coated granules are then passed through a 24-mesh sieve and a 42-mesh sieve to regulate the grain size.
Sample 3–7: Coated granules of 5-Fu and PANA (products of this invention)
 The sample, shown in the following table, were prepared in the same way as Sample 2 except that the amount of PANA and mannitol were changed.

| Sample No. | Name | PANA (parts) | Mannitol (parts) |
|---|---|---|---|
| 3 | 5-Fu/PANA(10%) coated granules | 10 | 72 |
| 4 | 5-Fu/PANA(20%) coated granules | 20 | 62 |
| 5 | 5-Fu/PANA(30%) coated granules | 30 | 52 |
| 6 | 5-Fu/PANA(50%) coated granules | 50 | 32 |
| 7 | 5-Fu/PANA(80%) coated granules | 80 | 2 |

2. Experimental method 2-1. Comparison of serum concentration of 5-Fu
 0.05 ml of a suspension of rate ascites hepatoma AH-66 cells ($1 \times 10^8$ cells/ml) was injected into the greater curvature of glandular stomach of rats (Donryu ô, 9-week-old, weighing 170–185 gr), and the test was carried out 7 days later. 5-Fu was administered, perorally in all cases, at the dose of 50 mg/kg. The solid-form preparations were dispersed in water and then immediately administered. Water was used such that its total amount would become 5 ml.
 Each test group was composed from 6 rats.
 Blood was collected by canulation into the carotid artery one hour after administration of the medicinal composition, and the determination of serum concentration of 5-Fu was made by bioassay.

2-2. Concentration of 5-Fu in transplanted tumor in stomach of rats
 The stomach of each rat used in test 2-1 was removed and washed well with a physiological saline solution, and then the gastric tumor was separated from the stomach and weighed and then homogenized after adding an equivalent volume of a phosphate buffer and further an equivalent volume of 15% trichloroacetic acid solution, and after centrifugation, the supernatant was neutralized and 5-Fu concentration in the supernatant was determined by bioassay.

2-3. 5-Fu concentration in normal rat stomach
 Tested in the same manner as 2-2.

2-4. Effect of 5-Fu on the growth of tumor transplanted in stomach
 AH-66 cells were transplanted after the manner of 2-1 to the greater curvature of glandular stomach of rats (Donryu ô, 9-week-old, weighing 170–180 gr; each group comprising 15 rats), and after the lapse of 24 hours, each specimen was administered once a day for the period of 10 days, and one day after the completion of administration, the tumor in each rat was enucleated and weighed to determine the inhibitory effect of each specimen on the growth of the tumor. 5-Fu was given at the dose of 30 mg/kg. The total amount of water used for dispersion was 3 ml.

2-5. Effect of 5-Fu on the growth of tumor subcutaneously transplanted in right inguinal site
 The experiment was conducted after the manner of 2-4 by transplanting the AH-66 cells to the right inguinal site of rats.

2-6. Toxicity test 2-6-1. Change of body weight
 Each specimen of 5-Fu was administered in the same manner as 2-4 to the rats (Donryu ô, 9-week-old, weighing 170–180 gr; each group consisting of 5 rats), and the change of body weight was checked.

2-6-2. Change of the member of leukocytes
 The number of leukocytes in each rat tested in 2-6-1 was counted.

2-6-3. Occult blood test of excrements

The occult blood test was made on the rats used in 2-6-1 after 0 time, 5 times and 10 times of administrations. 2-6-4. Change of weight of thymus and spleen The weight of thymus and spleen of rats used in 2-6-1 was measured after completion of 10 times of administration and after undergoing the tests of 2-6-1 to 2-6-3.

3. Experimental results 3-1. Comparison of 5-Fu concentration in normal stomach serum and tumor transplanted in stomach The results of tests 2-1, 2-2 and 2-3 are shown in Table 1.

TABLE 1

| Sample No. | Sample | 5 Fu concentration 1 hr after administration (mcg/ml) ± SD | | | Selectivety index | |
|---|---|---|---|---|---|---|
| | | Serum (A) | Transplanted Tumor (B) | Normal stmach (C) | B/A | C/A |
| 1 | 5-Fu solution | 2.14 ± 0.36 | 4.76 ± 0.88 | 5.06 ± 1.01 | 2.22 | 2.36 |
| 2 | 5-Fu/PANA(5%) coated granules | 2.08 ± 0.66 | 12.05 ± 4.37 | 17.92 ± 5.18 | 5.79 | 8.62 |
| 3 | 5-Fu/PANA(10%) coated granules | 1.83 ± 0.17 | 39.14 ± 10.16 (14.82) | 63.37 ± 15.80 (26.68) | 21.39 (8.10) | 34.63 |
| 4 | 5-Fu/PANA(20%) coated granules | 1.04 ± 0.45 | 37.52 ± 3.11 | 52.02 ± 13.30 | 36.08 | 50.02 |
| 5 | 5-Fu/PANA(30%) coated granules | 0.95 ± 0.42 (1.68) | 10.58 ± 1.45 (21.27) | 20.30 ± 2.15 (39.35) | 11.14 (12.66) | 21.37 |
| 6 | 5-Fu/PANA(50%) coated granules | 1.97 ± 0.56 | 12.33 ± 2.82 | 21.91 ± 4.78 | 6.26 | 11.12 |
| 7 | 5-Fu/PANA(80%) coated granules | 2.19 ± 0.79 | 9.21 ± 1.19 (39.14) | 25.62 ± 3.05 (33.24) | 4.21 (17.87) | 11.70 |

As seen in the table 1, the concentration of 5 Fu in serum is generally low although it is scarcely affected by PANA, whereas the concentration of 5 Fu in the tumor transplanted in stomach is increased 2 to 8 times by PANA and the selectivety index is increased 2 to 16 times. The concentration in normal stomach is also increased by 3 to 12 times, with the selectivity index increasing by 4 to 21 times.

3-2. Effect of 5-Fu on the growth of tumor transplanted in stomach

The results are shown in Table 2 below.

TABLE 2

| Sample No. | Sample | Tumor weight (g) | Ratio to control* |
|---|---|---|---|
| 1 | 5-Fu solution | 0.285 ± 0.040 | 91% |
| 2 | 5-Fu/PANA(5%) coated granules | 0.261 ± 0.039 | 83% |
| 3 | 5-Fu/PANA(10%) coated granules | 0.230 ± 0.040 | 73% |
| 4 | 5-Fu/PANA(20%) coated granules | 0.241 ± 0.026 | 77% |
| 5 | 5-Fu/PANA(30%) coated granules | 0.215 ± 0.036 | 68% |
| 6 | 5-Fu/PANA(50%) coated granules | 0.228 ± 0.038 | 73% |
| 7 | 5-Fu/PANA(80%) coated granules | 0.235 ± 0.034 | 75% |

*Control: AH-66 in stomach tumors transplanted in stomach non-treated with 5-Fu preparation. The average tumor weight in the control group was 0.314 ± 0.040 gr.

As noted from Table 2, Specimens 2-7 obviously arrested growth of tumor in comparison with the 5-Fu solution.

3-3. Effect of 5-Fu on the growth of subcutaneous tumor at inguinal site

The results are shown in Table 3.

TABLE 3

| Sample No. | Sample | Tumor weight (g) | Ratio to control* |
|---|---|---|---|
| 1 | 5-Fu solution | 1.251 ± 0.202 | 60% |
| 2 | 5-Fu/PANA(5%) coated granules | 1.283 ± 0.196 | 61% |
| 3 | 5-Fu/PANA(10%) coated granules | 1.223 ± 0.235 | 59% |
| 4 | 5-Fu/PANA(20%) coated granules | 1.264 ± 0.217 | 61% |
| 5 | 5-Fu/PANA(30%) coated granules | 1.295 ± 0.221 | 62% |
| 6 | 5-Fu/PANA(50%) coated granules | 1.208 ± 0.208 | 58% |
| 7 | 5-Fu/PANA(80%) coated granules | 1.306 ± 0.172 | 63% |

*Control: Subcutaneous AH-66 tumors non-treated with 5-Fu preparation. The average tumor weight of the control group was 2.089 ± 0.159 gr.

As apparent from the table 3, there is no significant different in effect between Sample 1 and Samples 2-7.

3-4. Reduction of adverse effects

Change of body weight, change of the number of leukocytes, occult blood test and weight changes of thymus and spleen related to born marrow toxicity were measured.

The results are shown in Table 4.

TABLE 4

| Specimen No. | | 0 | 1 | 2 | 3 | 4 | 5 | 6 | 7 |
|---|---|---|---|---|---|---|---|---|---|
| Content | | Control | 5-Fu solution | 5-Fu/PANA (5%) coated granules | " (10%) " | " (20%) " | " (30%) " | " (50%) " | " (80%) " |
| Rate of body weight change | 0 day | 100 | 100 | 100 | 100 | 100 | 100 | 100 | 100 |
| | 5th day | 119 | 95 | 97 | 93 | 99 | 102 | 103 | 108 |
| | 10th day | 133 | 85 | 89 | 86 | 93 | 98 | 99 | 101 |
| Leukocytes $10^2$/mm$^3$ | | 127 ± 33 | 52 ± 12 | 61 ± 13 | 78 ± 20 | 73 ± 18 | 75 ± 16 | 82 ± 21 | 104 ± 28 |
| | 0 | — | 5 | 5 | 5 | 5 | 5 | 5 | 5 |

TABLE 4-continued

| Specimen No. | | | 0 | 1 | 2 | 3 | 4 | 5 | 6 | 7 |
|---|---|---|---|---|---|---|---|---|---|---|
| | day | ± | 0 | 0 | 0 | 0 | 0 | 0 | 0 | 0 |
| | | + | 0 | 0 | 0 | 0 | 0 | 0 | 0 | 0 |
| Occult blood test (N = 6) | 5 day | − | 5 | 2 | 2 | 4 | 3 | 2 | 5 | 4 |
| | | ± | 0 | 0 | 3 | 1 | 2 | 3 | 0 | 1 |
| | | + | 0 | 3 | 0 | 0 | 0 | 0 | 0 | 0 |
| | 10 day | − | 5 | 1 | 2 | 1 | 4 | 4 | 5 | 4 |
| | | ± | 0 | 2 | 2 | 3 | 1 | 1 | 0 | 1 |
| | | + | 0 | 2 | 1 | 1 | 0 | 0 | 0 | 0 |
| Relative weight ratio of spleen | | | 100 | 49 | 61 | 59 | 65 | 63 | 70 | 75 |
| Relative weight ratio of thymus | | | 100 | 16 | 25 | 28 | 29 | 36 | 38 | 44 |

The results of Table 4 are reviewed below severally.

3-4-1. Change of body weight

Samples 3–6 were less in the rate of decrease of body weight than Samples 1 and 2, and even an increase of body weight was seen in some groups, such as at 5th day in Sample 4, at 5th and 10th days in Sample 5 and at 5th day in Sample 6.

3-4-2. Decrease of the member of leukocytes

The number of leukocytes decreased in all specimens in comparison with the control, but in Samples 3–6, the degree of decrease was significantly less than Sample 1.

3-4-3. Occult blood test

As noted from the table 4, Samples 2–6 were slight in the degree of occult blood test and reduced in toxicity to the digestive organs.

3-4-4. Effect on weight of thymus and spleen

Both spleen and thymus were atrophied in all samples as compared with the control, but the degree of such atrophy was less in Samples 2–6 (5-Fu/PANA preparations) than in Sample 1.

4. Conclusion

From the results described above, it is apparent that the antitumor compositions according to this invention are higher in potency than the single 5-Fu preparation and also obviously lessened in adverse effects, indicating a high possibility of this invention to make a significant contribution to more effective medical treatment.

EXAMPLE 2 (ANIMAL EXPERIMENTS)

1. Preparation of samples

Sample 1: BLM complex (mixture of BLM-A and BLM-B obtained by fermentation) hydrochloride injection (control)

10 mg of BLM complex hydrochloride is dissolved in 600 μl of distilled water.

Sample 3: Peroral solution of BLM complex hydrochloride (control)

Prepared by making an aqueous solution of 4 mg/ml of BLM complex hydrochloride.

Sample 2: Injection of sulfate of BLM derivative where the terminal amino group of BLM is phenylethylaminopropylamino group (hereinafter referred to as PEAP-BLM) (control)

10 mg/ampule of PEAP-BLM sulfate is dissolved in 500 μl of distilled water.

Sample 4: Peroral solution of PEAP-BLM sulfate (control)

Prepared by making a 4 mg/ml aqueous solution of PEAP-BLM sulfate.

Sample 5: BLM complex/PANA (5%) coated granules (product of this invention)

5 parts of finely pulverized PANA having molecular weight of approximately 5,500,000 and passed through a 150-mesh sieve, 10 parts of BLM complex hydrochloride, 77 parts of mannitol and 3 parts of hydroxypropyl cellulose are mixed uniformly and the mixture is granulated by a granulator with 0.5 mm extruding pore diameter by using 25 parts of official ethanol, and these granules, after drying, are passed through a 24-mesh sieve and a 42-mesh sieve to regulate the grain size. The thus obtained granules are then coated with a coating solution comprising 5 parts of ethyl cellulose with viscosity of 10 c.p.s., 1 part of triacetin, 47 parts of ethanol and 47 parts of methylene chloride, the coating being performed such that 95 parts of said granules will become 100 parts in the finished form, and then the thus coated granules are passed through a 24-mesh sieve and a 42-mesh sieve to regulate the grain size.

Sample 6: PEAP-BLM sulfate/PANA(5%) coated granules (product of this invention)

Prepared in the same way as Sample 5 but by using PEAP-BLM sulfate as active compound.

Sample 7: Prepared in the same way as Sample 5 except for use of 20 parts of PANA and 62 parts of mannitol (product of this invention)

Sample 8: Similar to Sample 7 except that the active compound is PEAP-BLM sulfate (product of this invention)

Sample 9: Prepared in the same way as Sample 5 except for use of 50 parts of PANA and 28 parts of mannitol (product of this invention)

Sample 10: Similar to Sample 9 except that the active compound is PEAP-BLM sulfate (product of this invention)

2. Method of experiment 2-1. Distribution of BLM in stomach, tumor transplanted in stomach and blood of rats 0.025 ml of a suspension of rat ascites hepatoma AH-66 cells ($1 \times 10^8$ cells/ml) was injected to the greater curvature of glandular stomach of rats (Donryu ô, 7-week-old, weighing 155–170 gr), and 12 days after transplantation, each BLM preparation was administered at the dose of 50 mg/kg to the overnigh fasted rats, and the BLM concentrations in the stomach, tumor transplanted in stomach and blood were measured 1, 2 and 4 hours after administration.

Samples 1 and 2 were given by way of subcutaneous injection and all of the remaining samples were administered perorally. Any solid preparation was once dispersed in water and then administered. The total volume administered was 2.5 ml/100 gr (body weight).

Each sample for the determination of BLM was prepared in the following way.

The stomach was removed and washed well with a physiological saline solution, and then the tumor and normal stomach portion were separated and weighed and then homogenized after adding twice as much amount of 7.5% trichloroacetic acid solution, and after centrifugation, the supernatant was neutralized for the determination of BLM by bioassay. For determining the concentration of BLM in blood, blood was collected by canulation from the carotid artery into a centrifuge tube to which two drops of heparin solution had been added, and 2 ml of 7.5% trichloroacetic acid was added to 1 ml of blood, and after centrifugation, the supernatant was neutralized for the determination of BLM by bioassay. Each test group was composed of 6 rats.

3. Results of experiment 3-1. Comparison of BLM concentration in normal stomach, blood and tumor transplanted in stomach.
The results of experiment 2-1 are shown in Table 1.

TABLE 1

| Sample No. | Sample | Concentration in normal stmach mcg/g tissue | | | Concentration in tumor transplanted in stmach mcg/g tissue | | | Concentration in blood mcg/g | | |
|---|---|---|---|---|---|---|---|---|---|---|
| | | 1 hr | 2 hr | 4 hr | 1 hr | 2 hr | 4 hr | 1 hr | 2 hr | 4 hr |
| 1 | C*[1] injection (subcutaneous) | 3.2 ± 1.3 | n.d.*[3] | n.d. | 1.4 ± 0.2 | n.d. | n.d. | 60.2 | 15.3 | n.d. |
| 2 | P*[2] injection (subcutaneous) | 5.8 ± 1.7 | 2.1 ± 0.5 | " | 1.7 ± 0.4 | " | " | 55.7 | 18.6 | " |
| 3 | C solution (peroral) | 4.3 ± 1.5 | n.d. | " | 1.8 ± 0.5 | " | " | n.d. | n.d. | " |
| 4 | P solution (peroral) | 7.1 ± 1.9 | 2.5 ± 0.6 | " | 2.1 ± 0.7 | " | " | " | " | " |
| 5 | C and PANA 5% coated granules | 5.8 ± 2.1 | 13.6 ± 2.3 | 8.4 ± 1.7 | 5.6 ± 1.4 | 3.7 ± 0.3 | 4.1 ± 0.4 | " | " | " |
| 6 | P and PANA 5% coated granules | 9.3 ± 2.4 | 15.1 ± 2.8 | 11.6 ± 2.3 | 5.3 ± 1.2 | 4.5 ± 0.4 | 2.9 ± 0.3 | " | " | " |
| 7 | C and PANA 2% coated granules | 8.9 ± 2.3 | 7.5 ± 1.9 | 8.8 ± 2.1 | 3.9 ± 0.5 | 4.3 ± 0.4 | 2.8 ± 0.4 | " | " | " |
| 8 | P and PANA 2% coated granules | 11.1 ± 2.7 | 13.7 ± 2.2 | 9.8 ± 1.7 | 4.7 ± 0.4 | 5.2 ± 0.5 | 4.4 ± 0.5 | " | " | " |
| 9 | C and PANA 50% coated granules | 6.4 ± 1.9 | 9.1 ± 1.7 | 11.2 ± 2.4 | 5.1 ± 0.7 | 3.6 ± 0.3 | 4.2 ± 0.5 | " | " | " |
| 10 | P and PANA 50% coated granules | 7.8 ± 2.1 | 12.2 ± 2.1 | 14.2 ± 2.5 | 3.8 ± 0.4 | 4.8 ± 0.4 | 4.6 ± 0.4 | " | " | " |

(Notes)
*[1]: "C" indicated BLM complex.
*[2]: "P" indicated PEAP-PLM.
*[3]: "n.d." indicates concentration below the detectable limit.
The numerical figures in the table show the mean values and standard errors.

As noted from the above table, BLM in the perorally administered preparations including the products of this invention scarcely presents itself in the blood. On the other hand, as regards the BLM concentration in the tumor transplanted in stomach, it is non-detectable (below the detectable limit) in 2-hour and 4-hour periods in the case of administration in the form of an aqueous solution, whereas in the case of the products of this invention, such BLM concentration is 2 to 4 times higher in each of 1-hour, 2-hour and 4-hour periods. Likewise, the BLM concentration in the normal stomach is unnoticeable in 2-hour and 4-hour periods in the case of subcutaneous injection and peroral administration in the form of an aqueous solution, whereas the products of this invention maintain substantially unchanged concentration level throughout the test period and show a higher concentration level than in the former cases.

It is thus obvious that the antitumor preparations according to this invention are significantly increased in potency as compared with the conventional BLM injections and peroral solutions, so that a high expectation can be placed on this invention for its contribution to the art of medication.

EXAMPLE 3 (Preparation of composition coated granules)

10 parts of 5-Fu, 30 parts of PANA, 54 parts of mannitol and 2 parts of polyvinyl pyrrolidone are mixed uniformly, and this mixture is further added with 30 parts of a hydrous alcohol solution consisting of 10 parts of water and 90 parts of officinal ethanol, followed by uniform kneading. The kneaded mixture is granulated by an extrusion granulator with 0.6 mm extruding pore diameter, and the formed granules are dried and regulated in grain size by forcibly passing through a 16-mesh sieve and removing the fine granules or powdery particles which pass the 42-mesh.

Then the thus obtained granules are coated with a coating solution comprising 5 parts of ethyl cellulose (10 c.p.s.), 1 part of triaceton, 47 parts of isopropyl alcohol and 47 parts of methylene chloride such that 96 parts of said granules will become 100 parts in the finished (coated) form.

EXAMPLE 4 (Preparation of composition: powder)

10 parts of 5-Fu, 20 parts of PANA (24- to 42-mesh) and 70 parts of crystalline lactose are uniformly mixed to obtain a powder.

EXAMPLE 5 (Preparation of composition: granules)

10 parts of 5-Fu, 20 parts of PANA 61 parts of powdered lactose and 4 parts of hydroxypropyl cellulose are uniformly mixed, and this mixture is further added with 25 parts of officinal ethanol and evenly kneaded. The kneaded mixture is granulated by an extrusion granulator with 0.7 mm extruding pore diameter, then dried and regulated in grain size by passing through a 16-mesh sieve and removing the fine granules or powdery particles by a 28-mesh screen.

EXAMPLE 6 (Preparation of composition: tablets)

5 parts of 5-Fu, 10 parts of PANA, 23.5 parts of mannitol and 1.5 parts of hydroxypropylmethyl cellulose are uniformly mixed, followed by further addition of 10 parts of officinal ethanol and uniform kneading, and the kneaded mixture is granulated by a kneading granulator ("Speed Kneader ®" by Okada Seiko Co.), then dried and regulated in grain size by passing through a 20-mesh sieve and removing the fine particles which pass the 60-mesh.

Then 29 parts of crystalline cellulose (Avicel ® by Asahi Kasei Co.), 5 parts of calcium cellulose glycolate and 1 part of magnesium stearate are blended to 50 parts of said granules, and the blend is molded into tablets with weight of approximately 800 mg per tablet and hardness of 9 kg by using a pestle with diameter of 13 mm and radius of curvature of 15 mm.

EXAMPLE 7 (Preparation of composition: granules)

10 parts of 5-Fu, 30 parts of PANA, 58 parts of mannitol and 2 parts of polyvinyl pyrrolidone are uniformly mixed, followed by further addition of 30 parts of a hydrous alcohol solution consisting of 10 parts of water and 90 parts of officinal ethanol and uniform kneading. The kneaded mixture is granulated by an extrusion granulator with 0.7 mm extruding pore diameter, and the formed granules are dried and regulated in grain size by passing through a 16-mesh sieve and removing the fine granules or powdery particles which pass the 32-mesh. The thus obtained granules are called "first granules".

Then 98 parts of powdery sodium bicarbonate and 2 parts of polyvinyl pyrrolidone are uniformly mixed, followed by addition of 20 parts of anhydrous ethanol and uniform kneading, and the kneaded mixture is treated in the same manner as in the case of the first granules. The thus obtained granules are called "second granules".

Then 98 parts of powdery dl-tartaric acid and 2 parts of polyvinyl pyrrolidone are uniformly mixed, followed by addition of 20 parts of chloroform and uniform kneading, and the kneaded mixture is treated in the similar way to the first granules to obtain "third granules". Then these first, second and third granules are uniformly mixed in amounts of 50 parts, 25 parts and 25 parts, respectively, and packaged such that one package will weigh 1 gr.

EXAMPLE 8 (Preparation of composition coated granules)

10 parts of BLM-complex, 30 parts of PANA, 54 parts of mannitol and 2 parts of polyvinyl pyrrolidone are uniformly mixed, and the mixture is further added with 30 parts of a hydrous alcohol solution consisting of 10 parts of water and 90 parts of officinal ethanol and uniformly kneaded. The kneaded mixture is granulated by an extrusion granulator with 0.6 mm extruding pore diameter, followed by drying and grain size regulation. The latter is accomplished by forcibly passing the granules through a 16-mesh sieve and removing the fine granules or powdery particles which pass the 42-mesh.

The thus obtained granules are then coated with a coating solution comprising 5 parts of ethyl cellulose (with viscosity of 10 c.p.s.), 1 part of triacetin, 47 parts of isopropyl alcohol and 47 parts of methylene chloride, the coating being performed such that 96 parts of said granules will become 100 parts in the finished form.

EXAMPLE 9 (Preparation of composition: granules)

10 parts of PEAP-BLM, 20 parts of PANA, 61 parts of powdered lactose and 4 parts of hydroxypropyl cellulose are uniformly mixed, and the mixture is further added with 25 parts of officinal ethanol and uniformly kneaded. The kneaded mixture is then granulated by an extrusion granulator with 0.7 mm extruding pore diameter, and the obtained granules are dried and regulated in grain size by passing through a 16-mesh sieve and screening off the extremely fine granules or powdery particles by a 28-mesh sieve.

EXAMPLE 10 (Preparation of composition: tablets)

5 parts of BLM-complex, 10 parts of PANA, 23.5 parts of mannitol and 1.5 parts of hydroxypropylmethyl cellulose are uniformly mixed, followed by further addition of 10 parts of officinal ethanol and uniform kneading. The kneaded mixture is then granulated by a kneading granulator ("Speed Kneader" by Okada Seiko), and the obtained granules are dried and regulated in grain size by passing through a 2-mesh sieve and eliminating the fine grains or powdery particles which pass the 60-mesh.

Then 29 parts of crystalline cellulose (Avicel 101 ®) by Asahi Kasei), 5 parts of calcium salt of carboxymethyl cellulose and 1 part of magnesium stearate are blended to 50 parts of the above-said granules, and the blend is molded into tablets weighting approximately 800 mg per tablet and having hardness of 9 kg by using a pestle with diameter of 13 mm and curvature of 15 mm.

EXAMPLE 11 (Preparation of composition: granules)

10 parts of PEAP-BLM, 30 parts of PANA, 58 parts of mannitol and 2 parts of polyvinyl pyrrolidone are uniformly mixed, and the mixture is added with 30 parts of a hydrous alcohol solution consisting of 10 parts of water and 90 parts of officinal ethanol and uniformly kneaded. The kneaded mixture is granulated by an extrusion granulator with 0.7 mm extruding pore diameter and the obtained granules are dried and regulated in grain size by passing through a 16-mesh screen and eliminating the extremely fine granules or powdery particles which pass the 32-mesh. The thus obtained granules are called "first granules".

Then 98 parts of powdery sodium bicarbonate and 2 parts of polyvinyl pyrrolidone are uniformly mixed, followed by further addition of 20 parts of anhydrous ethanol and uniform kneading, and the kneaded mixture is treated in the same manner as the first granules. The thus obtained granules are called "second granules".

Then 98 parts of powdery dl-tartaric acid and 2 parts of polyvinyl pyrrolidone are uniformly mixed, followed by addition of 20 parts of chloroform and uniform kneading and further followed by the same treatment as the first granules, thereby obtaining the third granules. Then these first, second and third granules are uniformly blended in amounts of 50 parts, 25 parts and 25 parts, respectively, and packaged such that one package will weigh 1 gr.

What is claimed is:

1. A peroral antitumor composition containing an effective amount of 5-fluorouracil, a sufficient amount of an alkali metal salt of polyacrylic acid having molecular weight 1,000,000 to 10,000,000 to enhance absorption of said active compound into the gastrointestinal tumor site, and a pharmaceutical adjuvant or adjuvants.

2. The composition of claim 1 wherein an amount of the alkali metal salt of polyacrylic acid is 0.5 to 20 parts (by weight) per 1 part of the active compound.

3. The composition of claim 1 wherein the composition comprising 1 to 30% (by weight) of the active compound, 5 to 90% (by weight) of an alkali metal salt of polyacrylic acid and 94 to 2% (by weight) of the adjuvant.

4. The composition of claim 2 wherein an amount of the alkali metal salt of the polyacrylic acid is 1 to 8 parts (by weight) to 1 part (by weight) of the active compound.

5. The composition of claim 2 wherein the molecular weight of the alkali metal salt of polyacrylic acid is 3,000,000 to 6,000,000.

6. The composition of claim 2 wherein the alkali metal salt of polyacrylic acid is sodium polyacrylate.

7. The composition of claim 1 wherein said composition is prepared into granules coated with a coating which is insoluble in water but permeable to water.

8. A method for enhancing selective absorption of the active compound into the gastrointestinal tumor site in man or animal comprising perorally administering an effective amount of 5-fluorouracil to man or animal along with an alkali metal salt of polyacrylic acid having molecular weight 1,000,000 to 10,000,000 of an amount sufficient to induce desired enhancement of selective absorption of said active compound into the gastrointestinal tumor site.

9. The method of claim 8 wherein the amount of the alkali metal salt of the polyacrylic acid is 0.5 to 20 parts (by weight) per 1 part of the active compound.

10. The method of claim 9 wherein the alkali metal salt of polyacrylic acid is sodium polyacrylate.

11. The method of claim 8 wherein the said active compound and an alkali metal salt of polyacrylic are prepared with a pharmacentical adjuvant in the form of granules coated with a water-insoluble but water-permeable coating, and such granules are perorally administered to man or animal.

12. The method of claim 8 wherein the effective amount of the active compound is 0.1 to 10 mg/kg per day for man or animal.

* * * * *